United States Patent [19]

Bailey

[11] Patent Number: 4,582,060

[45] Date of Patent: Apr. 15, 1986

[54] TATTOOING TOOL AND NEEDLE ASSEMBLY FOR USE THEREIN

[75] Inventor: Ronald L. Bailey, St. Charles County, Mo.

[73] Assignee: Young Dental Manufacturing Company, Maryland Heights, Mo.

[21] Appl. No.: 673,277

[22] Filed: Nov. 20, 1984

[51] Int. Cl.[4] .................. A61D 1/00; B44B 5/00; B43K 5/00

[52] U.S. Cl. .................. 128/316; 81/9.22; 101/26; 101/19; 40/300

[58] Field of Search .............. 128/316, 62 A, 303.18, 128/303.19, 329 R, 329 A, 316, 1 R; 101/26, 19; 81/9.22; 40/300; 433/122, 124

[56] References Cited

U.S. PATENT DOCUMENTS

| 768,413 | 8/1904 | Wagner | 128/329 |
|---|---|---|---|
| 1,489,558 | 4/1924 | Timson | 40/300 |
| 1,781,362 | 11/1930 | Brigida | 128/303.19 |
| 1,865,610 | 7/1932 | Blair | 128/303.18 |
| 2,023,563 | 12/1935 | Willison | 128/303.19 |
| 2,126,777 | 8/1938 | Holt | 101/26 |
| 3,552,022 | 1/1971 | Axelsson | 433/122 |
| 3,633,584 | 1/1972 | Farrell | 128/316 |
| 4,214,490 | 7/1980 | Chizek | 40/300 |
| 4,416,279 | 11/1983 | Lindner et al. | 128/329 R |
| 4,437,361 | 3/1984 | Steckel et al. | 128/316 |
| 4,452,243 | 6/1984 | Leopoldi et al. | 128/329 R |
| 4,488,550 | 12/1984 | Niemeijer | 40/300 |
| 4,508,106 | 4/1985 | Angres | 128/1 R |

FOREIGN PATENT DOCUMENTS

| EP82081 | 6/1983 | European Pat. Off. | 128/329 A |
| 1480290 | 4/1967 | France | 128/303.18 |

Primary Examiner—Gene Mancene
Assistant Examiner—James Hakomaki
Attorney, Agent, or Firm—Polster, Polster and Lucchesi

[57] ABSTRACT

A reciprocating tool in the nature of a dental handpiece is modified to carry a needle/cone assembly for use as a tattooing device. The needle/cone assembly includes a needle assembly trapped in a cone structure. The needle assembly includes a cap portion which is held by fingers in the handpiece to prevent rotation of the needle assembly, and a frangible neck which is broken on removal of the needle/cone assembly from the handpiece to prevent reuse of the needle assembly. A removable protective tube around the needles acts also as an insertion tool for the needle assembly.

20 Claims, 6 Drawing Figures

TATTOOING TOOL AND NEEDLE ASSEMBLY FOR USE THEREIN

BACKGROUND OF THE INVENTION

This invention relates to a motorized tool. It is particularly adapted for use in a precision tool for injecting a material into or below the skin, and most particularly for use in a tool for cosmetic tattooing of humans. It will be described in connection with such use, although its usefulness is not limited thereto.

Human tattooing is now used not only for decoration but also in a variety of cosmetic surgery techniques. For example, tattooing may hide scars or other skin blemishes, or it may be used to simulate natural skin coloring in surgical reconstructions. Tattooing techniques have recently been employed around individual eyelash follicles to simulate eye liner on the eyelids of patients who are unable to apply eye liner to their own eyelids.

Numerous devices have heretofore been used for human and animal tattooing. Commonly, these devices have included a set of parallel needles held together in a needle assembly, an ink reservoir, and power means for vibrating or oscillating the needle assembly through the ink reservoir and into the skin. All, however, have suffered from certain drawbacks. Particularly in the cosmetic surgery techniques now being carried out, the highest standards are required for the tattooing device, including extremely accurate control of needle position, smooth and steady operation, lack of rotation of the needle assembly, accurate metering of pigment, and extraordinary sterility of the needles.

One of the objects of the present invention is to overcome the drawbacks of prior art tattooing devices and meet these high standards.

Another object is to provide a needle/cone assembly for use in such a device.

Another object is to provide a reciprocating device and tool which prevent reuse of the tool.

Other objects will occur to those skilled in the art in light of the following description and accompanying drawings.

In accordance with one aspect of this invention, generally stated, a tattooing device is provided including a housing, a needle retainer in the housing, a drive means in the housing for reciprocating the needle retainer with respect to the housing, and a needle/cone assembly removably attached to the housing. The needle/cone assembly includes a cone structure and a needle structure slidably trapped in the cone structure. The cone structure is preferably threaded to the housing, and the needle structure is snap-fitted to the needle retainer for reciprocation with respect to the cone structure. The needle retainer preferably includes means for preventing rotation of the needle structure.

In accordance with another aspect of the invention, a device is provided for driving a single use tool. The device includes a housing, a tool retainer in the housing, a drive means in the housing for reciprocating the tool retainer with respect to the housing, and a tool structure attached to the tool retainer by a one-way fitting. The tool structure includes a part which is broken upon removal of the tool structure from the tool retainer, to prevent reuse of the tool structure.

In the preferred embodiment, the tool structure is part of an assembly including the tool and a carrier in which the tool is trapped. The carrier is threaded to the device housing. The tool is snap-connected to the tool retainer as the carrier is threaded onto the device housing, and a frangible portion of the tool is broken as the carrier is threaded off the device housing. Preferably, the tool is a needle assembly. Also in the preferred embodiment, the carrier is a cone assembly including a frustoconical portion at its lower end and a cylindrical upper chamber in which a shoulder of the needle assembly is trapped.

In accordance with another aspect of the invention, a needle/cone assembly is provided for use in a tattooing device, the tattooing device having a housing and a needle retainer in the housing, the needle/cone assembly comprising means for removably attaching the needle/cone assembly to the housing, a cone structure and a needle structure slidably trapped in the cone structure. The needle structure preferably includes a frangible portion which is broken as the needle/cone assembly is removed from the device housing. The needle structure preferably is a needle assembly including a plurality of needles carried by a needle carrier. The needle structure is snap-fitted to the needle retainer for reciprocation with respect to the cone structure. The cone structure is preferably threaded to the housing. The needle carrier includes an upper cap portion which is adapted to be held by the needle retainer, and the frangible portion of the needle structure is a neck between the cap portion and the needles. Also in the preferred embodiment, the needle/cone assembly includes a frustoconical portion at its lower end and a cylindrical upper chamber in which a shoulder of the needle assembly is trapped.

A protective tube around the needles engages the lower end of the needle carrier and is frictionally held by the frustoconical portion. The tube acts as an insertion tool when the needle/cone assembly is assembled to the housing, to insure that the cap portion of the needle assembly is securely snapped into the needle retainer.

Other aspects of the invention will be better understood in light of the following description of the preferred embodiment.

DESCRIPTION OF THE PREFERRED EMBODIMENT

Figure 1:
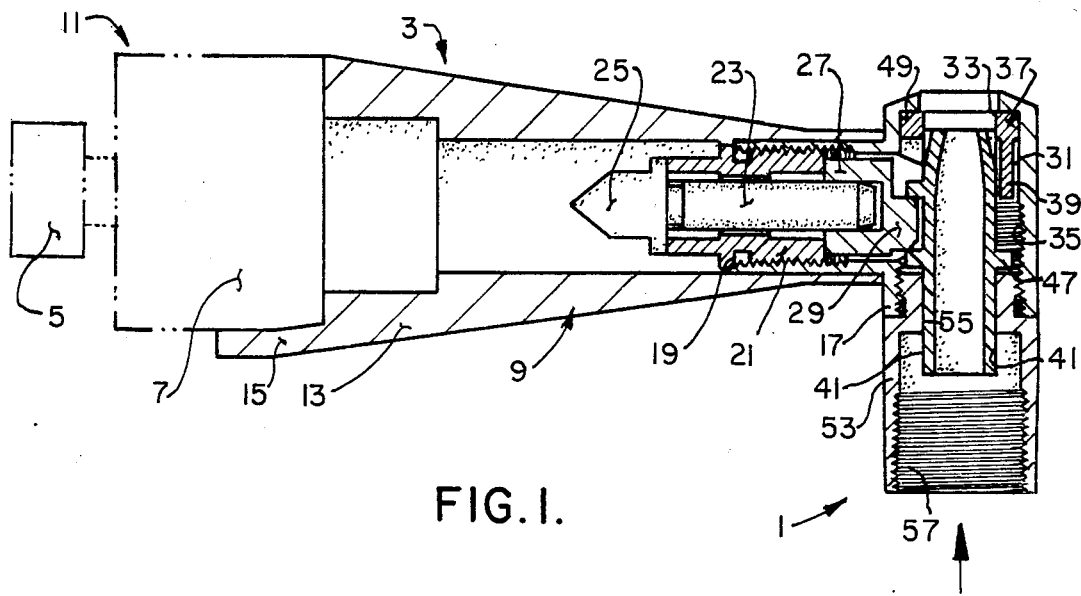
FIG. 1 is a view in cross section of a tattooing device of the present invention, with a needle/cone assembly of the invention separated from a drive housing.
Figure 2:
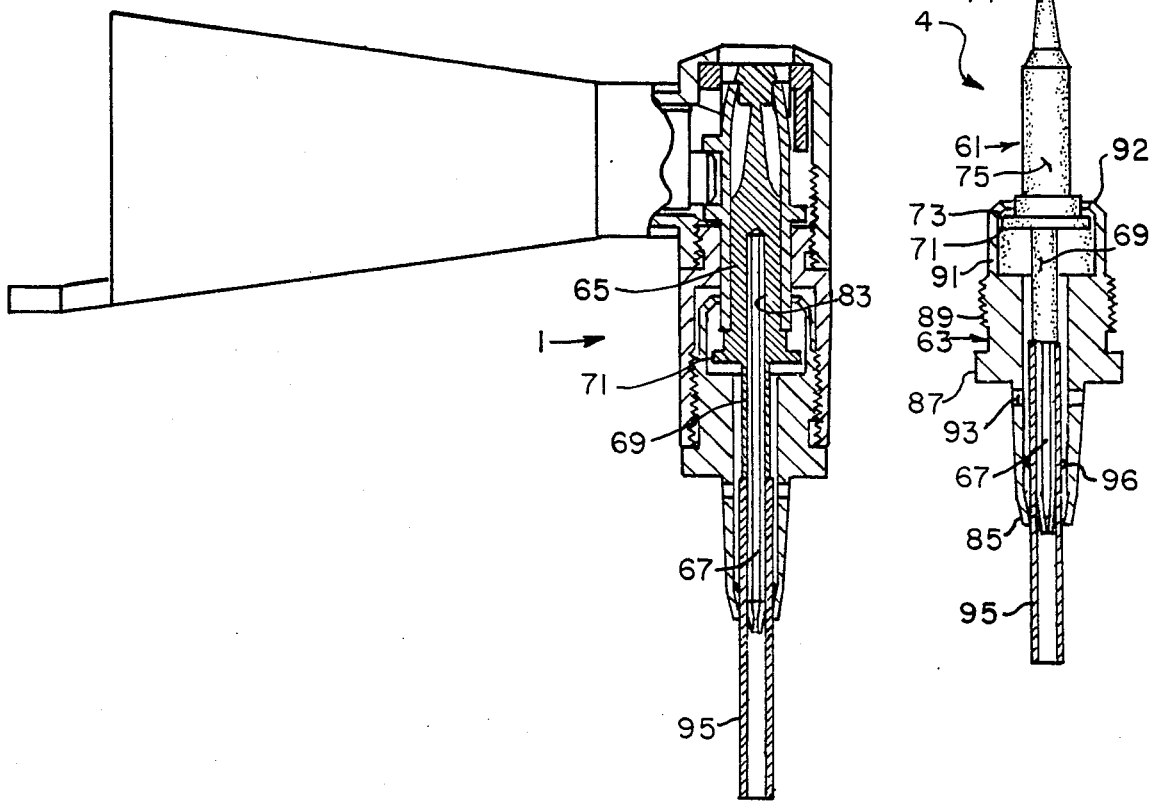
FIG. 2 is a view in partial cross section of the device of FIG. 1, with the needle/cone assembly assembled to the drive housing, and the needles in an extended position.
Figure 3:
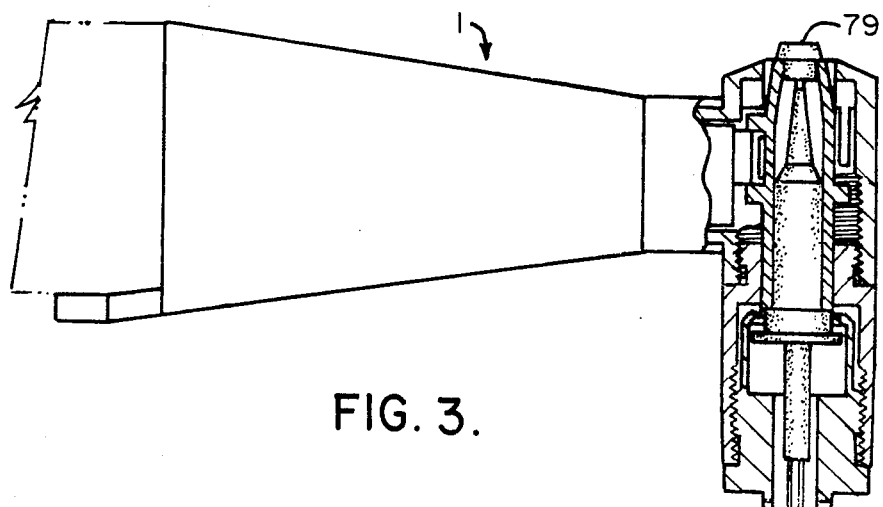
FIG. 3 is a view in partial cross section of the device of FIGS. 1 and 2, corresponding to FIG. 2, with a protective tube removed and with the needles in a retracted position.
Figure 4:
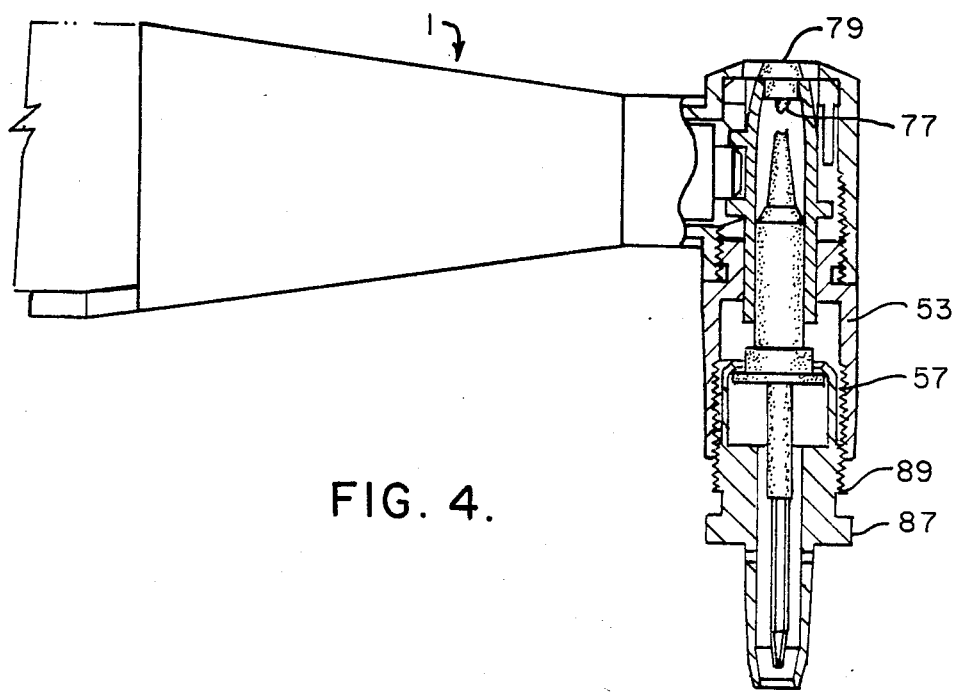
FIG. 4 is a view in partial cross section of the device of FIGS. 1-3, corresponding to FIGS. 2 and 3, with the needle/cone assembly partially removed from the drive housing, and a with a frangible neck portion of the needle/cone assembly broken to prevent reuse of the assembly.

Referring now to the drawings, reference numeral 1 indicates one illustrative embodiment of tattooing tool embodying the present invention. The tool 1 includes a motor-driven dental handpiece 3 and a needle/cone assembly 4.

The handpiece 3 includes a motor 5, a gear drive 7, and a modified reciprocating head 9. The motor 5 may be of any standard type, such as air-powered or electrical, and is preferably an electric motor operating at a nominal speed of about 15,000 revolutions per minute. The gear drive 7 may be a standard dental handpiece drive, typically having a gear ratio of 1:1. The modified head 9 may be similar to the head shown in U.S. Pat. No. 3,552,022 to Axelsson, and will be described in greater detail hereinafter. The motor 5, drive 7 and head 9 are contained in separate housings all of which are connected to each other by standard fittings to form a handpiece having a housing indicated generally at 11.

The head 9 includes a generally cylindrical housing 13 having at one end a standard connector 15 for connecting the head 9 to the drive 7. At its free end, the cylindrical housing 13 communicates with a perpendicular oscillator housing 17.

An oscillator mechanism 19 is threaded into the free end of the head housing 13 as shown in FIG. 1. The oscillator mechanism 19 includes an oscillator bearing 21, a shaft 23 in the bearing 21, a connector 25 on the shaft 23 for drivingly connecting the shaft 23 to the drive 7, and a cam 27 on the free end of the shaft 23. The cam 27 includes an eccentric lug 29 extending into the oscillator housing 17.

The oscillator housing 17 includes a cylindrical bore 31 having a step 33 at its rearward end and internal threads 35 at its forward end. A bearing 37 is tightly fitted in the bore 31, against the step 33. The bearing 37 includes a depending tail 39. A retaining tube 41 is slidably mounted in the bearing 37. As shown in greater detail in FIGS. 5 and 6, the retaining tube 41 is in the form of a tube having a forward annular rib 45 and a rearward annular rib 47, spaced apart sufficiently to receive the lug 29 between them. The rearward rib 47 is cut away to form a flat 49 which cooperates with the tail 39 on the bearing 37, thereby preventing rotation of the retaining tube 41 in the bearing 37. The retaining tube 41 is preferably formed of stainless steel.

As thus far described, the device 1 is a dental handpiece of a type sold by Young Dental Manufacturing Company as its DAWN EVA handpiece.

Figure 6:
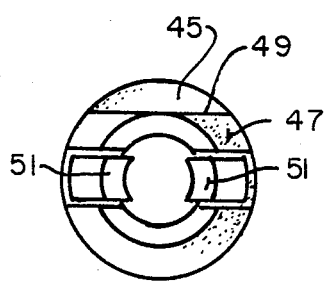
FIG. 6 is an end view of the needle retaining tube of FIG. 5 taken along line 6—6 of FIG. 5.
Figure 5:
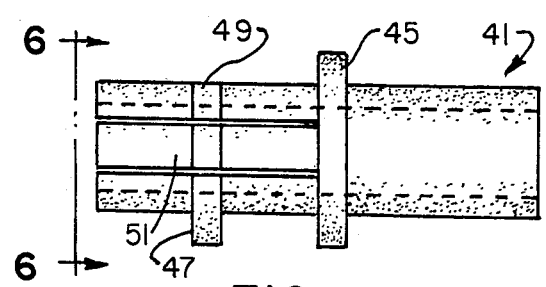
FIG. 5 is a view in side elevation of a needle retaining tube of the device of FIGS. 1-4.

The retaining tube 41, as shown in FIGS. 5 and 6, is modified by four longitudinal cuts extending from the rearward end of the retaining tube 41 to the forward rib 45 to form a pair of fingers 51. The fingers 51 are bent inwardly at their free ends.

An adapter 53 is threaded into the forward end of the oscillator housing 17. The rearward end of the adapter 53 includes an internal bearing 55 for the retaining tube 41. The forward end of the adapter 53 includes internal threads 57. The adapter 53 is made of stainless steel.

The needle/cone assembly 4 includes a needle assembly 61 and a cone structure 63. The needle assembly 61 includes a needle carrier 65 and three needles 67 carried by the carrier 65. The carrier 65 has a thin tubular forward part 69, an annular shoulder 71, a rearwardly-facing abutment 73, a body part 75, a thin frangible neck 77, and a cap part 79 having a rim 81. A blind axial bore 83 extends through the forward end of the carrier 65 into the body part 75. The three needles 67 are accurately aligned with each other in the form of an equilateral triangle, are fitted snugly into the bore 83, and are glued into the bore 83. The needle carrier 65 is machined from aluminum. The needles are nickel-plated carbon steel.

The cone structure 63 includes a frustoconical part 85 at its forward end, a collar part 87, a threaded plug part 89, and a rearward cylinder 91. The frustoconical part 85 is turned inwardly somewhat at its forward, free, end to form an ink reservoir. Breather holes 93 are provided at the rear of the frustoconical part 85. The cone structure 63 is formed of aluminum.

The needle assembly 61 is assembled to the cone structure 63, with the shoulder 71 in the cylinder 91 of the cone structure 63 and with the needles in the frustoconical part 85. The entire free rearward edge of the cylinder part wall is swaged inwardly as shown at 92, to trap the needle assembly shoulder 71 in the cylinder 91. The shoulder 71 is somewhat smaller than the inside diameter of the cylinder 91, to permit free reciprocation of the needle assembly in the cone structure.

An installation tube 95 is inserted into the frustoconical part 85 of the cone structure 63 and abuts the forward end of the needle carrier 65. The tube is pinched slightly out of round, as shown at 96, to hold it snugly in the frustoconical part, with its end pushing needle assembly to its rearward-most position in the cone structure. The tube 95 performs the dual function of protecting the needles 67 and aiding in the installation of the needle/cone assembly as described hereinafter. The installation tube 95 is made of stainless steel.

The needle/cone assembly 4, including the installation tube 95, is assembled, sterilized, and packaged in a sterile container.

In use, the needle/cone assembly 4 is removed from its packaging and inserted into the adapter 53 and oscillator housing 17. The threads 89 on the cone structure 63 are threaded into the threads 57 until the collar part 87 abuts the forward end of the adapter 53. As the cone structure 63 is threaded onto the head 9, the cap 79 on the needle carrier 61 is forced between the fingers 51 of the needle retaining tube 41. To ensure complete insertion of the needle assembly 61 into the retaining tube 41, the installation tube 95 is pushed rearwardly into the oscillator housing 17 before the tube 95 is removed. When the needle assembly 61 is completely inserted into the retaining tube 41, the abutment 73 on the needle assembly 61 engages the forward end of the retaining tube 41, and the fingers 51 tightly engage the cap 79, on the forward side of the rim 81. The body 75 of the needle carrier 65 fits snugly in the retaining tube 41. The fingers 51 perform the dual functions of locking the needle assembly axially with respect to the retainer tube 41 and of locking the needle assembly 61 against rotation. Upon application of a rotational force on the needle assembly 61, the stainless steel fingers 51 tend to dig into the softer aluminum to provide positive locking.

The tattooing device 1 is used in a conventional manner. Rotation of the motor 5 is transmitted through the drive 7 and connector 25 to the cam 27. The cam lug 29 reciprocates the retaining tube 41 at approximately 15,000 cycles per minute, thereby causing the needles 67 to be driven into and out of the frustoconical part 85.

The frustoconical part 85 is dipped in ink in a conventional manner, and the ink is held in the frustoconical part and carried on the tips of the needles 67. The breather holes 93 prevent the ink from being drawn into the cylinder 91. At the maximum forward stroke, the needles 67 extend about 1.5 millimeters from the end of the frustoconical part 85.

When a particular tattooing job has been completed, the needle/cone assembly 4 is unscrewed from the adapter 53. When the needle/cone assembly is backed out partially, the turned edge 92 of the cylinder 91 engages the shoulder 71. Continued unscrewing of the needle/cone assembly 4 causes the neck 77 to be snapped. The cap 79 is then able to fall out of the rearward opening of the oscillator housing 17, when it is pushed by a new needle/cone assembly's being inserted into the device 3.

It will be seen that the position of the needles is accurately controlled by the bearings 37 and 55, the fit of the needle carrier 65 in the retaining tube 41, and the secure permanent bonding of the needles in the bore 83 of the needle carrier 65. In use, the needle assembly does not touch the cone structure. Because the needle/cone assembly may be pre-sterilized and requires no handling of the needles during assembly, sterility is easily maintained. Automatic breakage of the frangible neck 77 ensures that needles, once removed, will not be reused. The accidental use of dull or unsanitary needles is thus prevented. The neck may easily be made strong enough for ordinary use, yet readily breakable upon removal of the needle/cone assembly. Should the neck break in use, the needles would no longer be driven, but would not fall out of the device.

Numerous variations in the tool and needle assembly of the present invention, within the scope of the appended claims, will occur to those skilled in the art in light of the foregoing disclosure. For example, other single use tools could be substituted for the needle assembly. Other drive devices could be used. Other materials may be employed. These variations are merely illustrative.

I claim:

1. In a tattooing device including a housing, a needle retainer in the housing, and a drive means in the housing for reciprocating the needle retainer with respect to the housing, the improvement comprising a needle/cone assembly removably attached to the housing, the needle/cone assembly comprising a cone structure, means for removably attaching the cone structure to the housing, a needle structure, the needle structure being reciprocatably mounted in the cone structure, means for trapping the needle structure in the cone structure, and connecting means for connecting the needle structure to the needle retainer.

2. The improvement of claim 1 wherein the needle structure is snap-fitted to the needle retainer for reciprocation with respect to the cone structure.

3. The improvement of claim 1 wherein the needle retainer is tubular and wherein the connecting means comprise an enlarged cap part on the needle structure and finger means at an upper end of the needle retainer for engaging the cap part, the needle structure further including at least one needle extending below the lower end of the needle retainer.

4. The improvement of claim 3 wherein the needle structure includes a frangible part between the cap part and the at least one needle, the finger means on the needle retainer engaging the cap part sufficiently tightly that removal of the needle/cone assembly from the housing breaks the frangible part.

5. The improvement of claim 1 wherein the cone structure includes a frustoconical portion at its lower end and a cylinder part, the means for trapping the needle structure in the cone structure comprising an enlarged part on the needle structure in the cylinder part of the cone structure, and means at the upper end of the cylinder part cooperative with the enlarged part to trap the needle structure in the cone structure.

6. The improvement of claim 1 wherein the means for removably attaching the cone structure to the housing comprise cooperating threads on the housing and on the cone structure.

7. The improvement of claim 1 wherein the needle structure includes a frangible part, the connecting means engaging the needle structure sufficiently tightly that removal of the needle/cone assembly from the housing breaks the frangible part.

8. In combination, a device comprising a housing, a tool retainer in the housing, and a drive means in the housing for reciprocating the tool retainer with respect to the housing; a tool comprising a tool structure and a tool carrier in which the tool structure is reciprocable; one-way attachment means for attaching the tool structure to the tool retainer by a one-way fitting, means for removably attaching the tool carrier to the housing, and means in the tool structure for rendering the tool structure unusable upon removal of the tool carrier from the housing.

9. The combination of claim 8 wherein the means in the tool structure for rendering the tool structure unusable upon removal of the tool carrier from the housing is a part which is broken upon removal of the tool structure from the tool retainer.

10. The combination of claim 9 wherein the carrier is threaded to the device housing, the tool is snap-connected to the tool retainer as the carrier is threaded onto the device housing, and a frangible portion of the tool is broken as the carrier is threaded off the device housing.

11. A needle/cone assembly for use in a tattooing device having a housing and a needle retainer in the housing, the needle/cone assembly comprising a cone structure, quick-connect means on the cone structure for removably attaching the cone structure to the device housing, a needle structure reciprocatable in the cone structure, and means for permanently trapping the needle structure in the cone structure.

12. The needle/cone assembly of claim 11 wherein the needle structure includes means rendering the needle structure unusable as the needle/cone assembly is removed from the device housing.

13. The needle/cone assembly of claim 12 wherein the needle structure is a needle assembly including a plurality of needles carried by a needle carrier, the means rendering the needle structure unusable being provided in the needle carrier.

14. The needle/cone assembly of claim 13 wherein the needle carrier includes an upper cap part, the upper cap part including means interengageable with the needle retainer in the device for snap-fitting the needle assembly to the needle retainer for reciprocation with respect to the cone structure.

15. The needle/cone assembly of claim 13 wherein the cone structure includes a frustoconical portion at its lower end and a cylinder part, the means for trapping the needle structure in the cone structure comprising an enlarged part on the needle structure in the cylinder part of the cone structure, and means at the upper end of the cylinder part cooperative with the enlarged part to trap the needle structure in the cone structure.

16. The needle/cone assembly of claim 14 wherein the means rendering the needle structure unusable is a frangible part of the needle carrier.

17. The needle/cone assembly of claim 11 wherein the means for trapping the needle structure in the cone structure comprises an enlarged part on the needle structure and means at an upper end of the cone part cooperative with the enlarged part to trap the enlarged part of the needle structure in the cone structure.

18. The needle/cone assembly of claim 17 wherein the quick-connect means on the cone structure comprise screw threads.

19. The needle/cone assembly of claim 11 further including a protective tube surrounding the lower end of the needle structure and frictionally held by the frustoconical part.

20. The needle/cone assembly of claim 19 wherein the tube engages an abutment on the needle structure and acts as an insertion tool when the needle/cone assembly is assembled to the housing, to insure that the cap portion of the needle assembly is securely pushed into the needle retainer.

* * * * *